United States Patent [19]

Berg

[11] Patent Number: 5,417,812
[45] Date of Patent: May 23, 1995

[54] SEPARATION OF ETHYL BENZENE FROM XYLENES BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 179,182

[22] Filed: Jan. 10, 1994

[51] Int. Cl.6 .......................... B01D 3/36; C07C 7/06
[52] U.S. Cl. ........................................ 203/60; 203/63; 585/805; 585/807; 585/864; 585/866
[58] Field of Search .................... 203/60, 63; 585/864, 585/866, 805, 807

[56] References Cited

U.S. PATENT DOCUMENTS

| 2,848,387 | 8/1958 | Glazier et al. | 203/60 |
| 4,292,142 | 9/1981 | Berg | 203/51 |
| 4,299,668 | 11/1981 | Berg | 203/63 |
| 5,135,620 | 8/1992 | Brown | 203/57 |

Primary Examiner—Wilbur Bascomb, Jr.

[57] ABSTRACT

Ethyl benzene is difficult to separate from xylenes by conventional distillation or rectification because of the proximity of their boiling points. Ethyl benzene can be readily separated from xylenes by azeotropic distillation. Effective agents for separating ethyl benzene from p-xylene are methyl formate, n-butanol and cyclopentanol; from p-xylene and m-xylene, n-butanol.

3 Claims, No Drawings

SEPARATION OF ETHYL BENZENE FROM XYLENES BY AZEOTROPIC DISTILLATION

FIELD OF THE INVENTION

This invention relates to a method for separating ethyl benzene from p-xylene and/or m-xylene using certain organic compounds as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or both of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

Ethyl benzene boils at 136.2° C., p-xylene at 138.4° C. and m-xylene at 139.1° C. The closeness of their boiling points gives ethyl benzene from p-xylene a relative volatility of 1.06. Table 1 shows the relative volatility required to get 99% purity. By straight rectification, 211 actual plates are required for the ethyl benzene—p-xylene separation but with an azeotropic agent that increases the relative volatilty to 1.3 only 47 actual plates are required.

TABLE 1

Theoretical and Actual Paltes Required vs. Relative Volatility for Ethyl Benzene - Xylenes Separation

| Relative Volatility | Theoretical Plates Required At Total Reflux, 99% Purity | Actual Plates Required, 75% Efficiency |
| --- | --- | --- |
| 1.06 | 158 | 211 |
| 1.25 | 42 | 56 |
| 1.3 | 35 | 47 |

OBJECTIVE OF THE INVENTION

The object of this invention is to provide a process or method of azeotropic distillation that will enhance the relative volatility of ethyl benzene from xylenes in their separation in a rectification column. It is a further object of this invention to identify organic compounds which in addition to the above constraints, are stable, can be separated from ethyl benzene and recycled to the azeotropic column and reused with little decomposition.

SUMMARY OF THE INVENTION

The objects of this invention are provided by a process for separating ethyl benzene from p-xylene and/or m-xylene which entails the use of certain organic compounds as the agent in azeotropic distillation.

DETAILED DESCRIPTION OF THE INVENTION

TABLE 2

Effective Azeotropic Distillation Agents

| Compounds | Relative Volatility, Ethyl Benzene - p-Xylene | Relative Volatility, Ethyl Benzene - m-Xylene |
| --- | --- | --- |
| Methyl formate | 1.23 | |
| n-Butanol | 1.27 | 1.32 |
| Cyclopentanol | 1.31 | 1.26 |

I have discovered that certain organic compounds will greatly improve the relative volatility of ethyl benzene to p-xylene and/or m-xylene and permit the enhanced separation of ethyl benzene from p-xylene and/or m-xylene by rectification. Table 2 lists the compounds that I have found to be effective. To separate ethyl benzene from p-xylene, the compounds are methyl formate, n-butanol and cyclopentanol. To separate ethyl benzene from p-xylene and m-xylene, the compound is n-butanol. To separate ethyl benzene from m-xylene, the compounds are n-butanol and cyclopentanol.

THE USEFULNESS OF THE INVENTION

The usefulness or utility of this invention can be demonstrated by referring to the data presented in Tables 1 and 2. All of the successful agents show that ethyl benzene can be separated from p-xylene and/or m-xylene by means of azeotropic distillation in a rectification column and that the ease of separation as measured by relative volatility is considerable.

WORKING EXAMPLES

Example 1

Eighty grams of ethyl benzene, 20 grams of p-xylene and 50 grams of cyclopentanol were charged to a vapor-liquid equilbrium still and refluxed for twelve hours. Analysis indicated a vapor composition of 81% ethyl benzene, 19% p-xylene; a liquid composition of 76.5% ethyl benzene, 23.5% p-xylene. This is a relative volatility of 1.31.

Example 2

Seventy-five grams of ethyl benzene, 75 grams of p-xylene and 100 grams of methyl formate were placed in the stillpot of a 7.3 theoretical plate glass perforated plate rectification column and refluxed for two hours. The overhead composition was 83.2% ethyl benzene, 16.8% p-xylene; the bottoms composition was 52% ethyl benzene, 48% p-xylene. This is a relative volatility of 1.23.

Example 3

Forty grams of ethyl benzene, 60 grams of p-xylene, 20 grams of m-xylene and 100 grams of n-butanol were placed in the stillpot of a 7.3 theoretical plate glass perforated plate rectification column and refluxed for eight hours. The overhead composition was 81.7% ethyl benzene, 14.7% p-xylene and 3.6% m-xylene; the bottoms composition was 41.8% ethyl benzene, 43.9% p-xylene and 14.3% m-xylene. This is a relative volatility of ethyl benzene to p-xylene of 1.27 and of p-xylene to m-xylene of 1.04 which shows that this agent will separate ethyl benzene from a mixture with p-xylene and m-xylene.

I claim:

1. A method for recovering ethyl benzene from a mixture of ethyl benzene and p-xylene which comprises distilling a mixture of ethyl benzene and p-xylene in the presence of an azeotrope forming agent, recovering the ethyl benzene and the azeotrope forming agent as overhead product and obtaining the p-xylene as bottoms product, wherein said azeotrope forming agent consists of one material selected from the group consisting of methyl formate, n-butanol and cyclopentanol.

2. A method for recovering ethyl benzene from a mixture of ethyl benzene, p-xylene and m-xylene which comprises distilling a mixture of ethyl benzene, p-xylene and m-xylene in the presence of an azeotrope forming agent, recovering the ethyl benzene and the azeotrope forming agent as overhead product and obtaining the p-xylene and the m-xylene as bottoms product, wherein said azeotrope forming agent is n-butanol.

3. A method for recovering ethyl benzene from a mixture of ethyl benzene and m-xylene which comprises distilling a mixture of ethyl benzene and m-xylene in the presence of an azeotrope forming agent, recovering the ethyl benzene and the azeotrope forming agent as overhead product and obtaining the m-xylene as bottoms product, wherein said azeotrope forming agent consists of one material selected from the group consisting of n-butanol and cyclopentanol.

* * * * *